(12) United States Patent
Colgan et al.

(10) Patent No.: US 9,041,931 B2
(45) Date of Patent: May 26, 2015

(54) SUBSTRATE ANALYSIS USING SURFACE ACOUSTIC WAVE METROLOGY

(75) Inventors: Michael Colgan, Flanders, NJ (US); Michael J. Kotelyanskii, Chatham, NJ (US); Christopher J. Morath, Basking Ridge, NJ (US); Humphrey J. Maris, Barrington, RI (US)

(73) Assignees: Rudolph Technologies, Inc., Flanders, NJ (US); Brown University, Providence, RI (US)

( * ) Notice: Subject to any disclaimer, the term of this patent is extended or adjusted under 35 U.S.C. 154(b) by 509 days.

(21) Appl. No.: 13/500,692

(22) PCT Filed: Oct. 8, 2010

(86) PCT No.: PCT/US2010/051996
§ 371 (c)(1),
(2), (4) Date: Aug. 20, 2012

(87) PCT Pub. No.: WO2011/044473
PCT Pub. Date: Apr. 14, 2011

(65) Prior Publication Data
US 2012/0309116 A1      Dec. 6, 2012

Related U.S. Application Data

(60) Provisional application No. 61/278,646, filed on Oct. 9, 2009.

(51) Int. Cl.
*G01N 21/00* (2006.01)
*G01N 29/24* (2006.01)
*G01N 29/04* (2006.01)
*G01N 29/12* (2006.01)
*B82Y 20/00* (2011.01)
(Continued)

(52) U.S. Cl.
CPC .......... *G01N 29/2418* (2013.01); *G01N 29/041* (2013.01); *G01N 29/12* (2013.01); *G01N 2291/0423* (2013.01); *B82Y 20/00* (2013.01); *B82Y 35/00* (2013.01); *G01Q 60/22* (2013.01)

(58) Field of Classification Search
USPC .................. 356/432, 630, 445, 450, 491, 301
See application file for complete search history.

(56) References Cited

U.S. PATENT DOCUMENTS 4,615,620 A     10/1986   Noguchi et al. .............. 356/378
4,710,030 A *  12/1987   Tauc et al. ..................... 356/432
(Continued)

FOREIGN PATENT DOCUMENTS

WO    WO 2005/097669 A1    10/2005

OTHER PUBLICATIONS

Ebbesen, T.W., et al., "Extraordinary optical transmission through sub-wavelength hole arrays", © Macmillin Publishers Ltd, 1998, pp. 667-669.

(Continued)

*Primary Examiner* — Sang Nguyen
(74) *Attorney, Agent, or Firm* — Merchant & Gould P.C.

(57) ABSTRACT

A system for imposing and analyzing surface acoustic waves in a substrate to determine characteristics of the substrate is disclosed. Optical elements and arrangements for imposing and analyzing surface acoustic waves in a substrate are also disclosed. NSOM's, gratings, and nanolight elements may be used to impose surface acoustic waves in a substrate and may also be used to measure transient changes in the substrate due to the passage of surface acoustic waves therethrough.

30 Claims, 8 Drawing Sheets

(51) Int. Cl.
*B82Y 35/00* (2011.01)
*G01Q 60/22* (2010.01)

(56) References Cited

U.S. PATENT DOCUMENTS

| | | | |
|---|---|---|---|
| 6,381,019 B1 | 4/2002 | Maris | 356/432 |
| 6,400,449 B2 | 6/2002 | Maris et al. | 356/72 |
| 6,818,907 B2 | 11/2004 | Stark | 250/492.1 |
| 7,046,365 B1* | 5/2006 | Aoshima et al. | 356/450 |
| 7,961,379 B2* | 6/2011 | Shigekawa et al. | 359/331 |
| 8,264,693 B2* | 9/2012 | Stoica et al. | 356/502 |
| 2001/0028460 A1* | 10/2001 | Maris et al. | 356/432 |
| 2002/0080355 A1* | 6/2002 | Maris | 356/432 |
| 2003/0020929 A1* | 1/2003 | Morath et al. | 356/630 |
| 2004/0188602 A1* | 9/2004 | Chinn et al. | 250/234 |
| 2004/0196453 A1* | 10/2004 | Some | 356/237.1 |
| 2004/0207850 A1* | 10/2004 | Kwak et al. | 356/432 |
| 2005/0023434 A1 | 2/2005 | Yacoubian | 250/200 |
| 2007/0078613 A1 | 4/2007 | Kurtin | 702/57 |
| 2007/0268478 A1 | 11/2007 | Wolf et al. | 356/73 |
| 2009/0032800 A1 | 2/2009 | Lee et al. | 257/13 |
| 2010/0157316 A1* | 6/2010 | Maris | 356/630 |

OTHER PUBLICATIONS

Liu, Zhaowei, et al., "Far-Field Optical Hyperlens Magnifying Sub-Diffraction-Limited Objects", Mar. 23, 2007, vol. 315, Science, 2 pgs.

* cited by examiner

SUBSTRATE ANALYSIS USING SURFACE ACOUSTIC WAVE METROLOGY

The present application is a national stage of PCT/US10/51996, filed Oct. 8, 2010, which claims the benefit of 61/278,646, filed Oct. 9, 2009.

TECHNICAL FIELD OF THE INVENTION

The present Invention relates to the analysis of structured substrates using optical pump/probe techniques that generate acoustic surface waves in a substrate under test.

BACKGROUND OF THE INVENTION

The present invention involves the generation and detection of very high frequency surface acoustic waves in a substrate. The structure of a substrate affects the frequency of the surface acoustic waves. Understanding the nominal structure of a substrate and modeling how variations in the nominal structure would affect the propagation of surface acoustic waves provides a key to decoding structure properties by observing surface acoustic wave propagation.

Surface acoustic waves such as Rayleigh waves and/or Lam waves are induced in a substrate such as stack of films on a semiconductor material or "film stack" using a typical pump/probe beam arrangement of the type embodied by Rudolph's MetaPULSE metrology system. A difference between a standard opto-acoustic system (as exemplified by U.S. Pat. No. 6,400,449) or a contact mask opto-acoustic system (as exemplified by U.S. Pat. No. 6,381,019) and the present invention is that a noncontact mask or pattern of light is projected onto the surface of the substrate, the pattern of light inducing a corresponding stress concentration pattern in the surface of the substrate. As will be appreciated, the stress concentrations propagate as acoustic waves both into the body of the substrate (longitudinal waves) as well as along the surface of the substrate. While it is possible to measure the propagation of acoustic waves "down" into the surface of a substrate, it is also possible to measure surface acoustic waves. It is also possible to measure the effects of surface and "depth" acoustic waves separately or together and to use this data to appreciate more and different features and characteristics of the substrate that is under test.

SUMMARY OF THE INVENTION

A noncontact optical system for the analysis of surface acoustic waves according to the present invention includes a pump element and a probe element. The pump element directs light or radiation to a surface of a substrate to induce a surface acoustic wave therein. The light or radiation incident on the substrate is selected to optimize the creation of the surface acoustic waves. A probe element directs light or radiation to the substrate to measure a transient change in a characteristic of the surface of the substrate due the passage of the surface acoustic wave. Light coded with information regarding the transient change in the surface of the substrate is returned to the probe element from the substrate and directed to a photodetector for measurement. The photodetector may be any useful photo sensor such as a charge-coupled device (CCD) or one or more photodiodes. A time delay element modifies the amount of time between when the surface acoustic wave is induced in the substrate and when light from the probe element is incident upon the substrate. A processor such as a computer having a logic and memory adapted to run computer programs obtains information concerning the transient change in the surface of the substrate from the photodetector and determines a characteristic of the substrate from this information using a lookup table, extrapolation, interpolation, or by using the information to otherwise obtain the desired characteristic from a model of the substrate.

The pump and probe elements may be fashioned from one or more NSOM devices operating in the near field, a grating or aperture array operating in the near field, or a nanolight element operating in the near or the far field. The composition of a nanolight element is described in more detail below. One characteristic of a nanolight element is that transmission of light therethrough is highly efficient, regularly approaching and exceeding what might otherwise be expected. Where properly constructed and implemented, the apertures or slits of a nanolight element can experience transmission efficiencies of greater than unity. Furthermore, nanolight elements, which may be formed of metamaterials, may experience less diffraction of transmitted/emitted light than would be expected using the equation $$d = \frac{\lambda}{2n\sin\alpha}.$$

Circular/cylindrical apertures or elongate slits, i.e. holes in the nanolight element through which light may be transmitted, may have a dimension of less than 100 nm or even less than 50 nm. These holes may be formed more or less individually, in pairs (one to act as a pump element and one to act as a probe element), or in arrays wherein multiple holes act as probe elements or pump elements.

In some embodiments, light or radiation is directed to a surface of a substrate and returned from a surface of the substrate by means of the pump and probe devices. In some instances these pump and probe elements may do double duty, acting as both pump and probe elements. However it is also the case that the probe element(s) may be used solely for directing light or radiation to the surface of a substrate. Separate collection optics consisting of refractive or reflective optical elements may be positioned to collect light returned from the surface of the substrate. In addition to obtaining information concerning transient optical changes in the surface of a substrate, the sensors associated with the probe elements of the system may obtain information about Rayleigh waves or LAM waves induced in the surface of the system. This information can also be used to determine characteristics of the substrate under test.

The pump and probe elements may be used in conjunction with a source of illumination to project different patterns of light or radiation onto the substrate. These patterns may be regular or may include different periods or pitches. Often these patterns and pitches are correlated to expected or nominal responses of the substrate to the application of surface acoustic waves. In one example, a pitch may be chose to substantially match a given wavelength of surface acoustic waves. In another example, the pitch may vary about a nominal or expected wavelength of surface acoustic waves in the substrate. Further, the combination of the pump or probe element with an illumination source may be used to project different k-vectors onto the surface of the substrate, simultaneously or serially. Differing periods, k-vectors and time delays between pump and probe allow a user to direct the processor to demodulate or determine numerous characteristics or features of a substrate. Note that time delays may be iterated step-wise through a range of selected time delays or may be continuously modified over the same range. In either instance, repetition of the application of a selected time delay may be useful.

In some embodiments, an illumination source is directly coupled to a pump or probe element, be they NSOM's, gratings or nanolight elements. In other embodiments, light is selectively directed between selected locations using a modulator. Selection may include directing light to one of a number of gratings or nanolight elements, each of which may define a different pattern or pitch for light that is to be incident upon the substrate. This technique may also be used to switch the illumination source between separate pump and probe elements.

The sensor and/or the collection optics may be provided with one or more optical elements or arrangements that help differentiate between the light or radiation used to induce a surface acoustic wave in a substrate (pump) and that used to measure a transient response to the surface acoustic wave in the substrate (probe). For example, the sensor may be polarization sensitive and block out or otherwise ignore pump light or radiation that has a given polarization state that is different from that of the probe light or radiation. Wavelength filtering may also work in this manner. Other ways of differentiating pump and probe light such as geometrically differentiating pump and probe light using angle of incidence or azimuthal angle may be used as well.

One use of a system for analyzing surface acoustic waves is in the manufacture of semiconductor devices. Other items or objects may also benefit from obtaining from such a system. Semiconductor devices are made using a number of photolithographic processes, many of which may be monitored using a system for analyzing surface acoustic waves. If characteristics of a semiconductor substrate that are not favorable to good performance are detected through analysis of surface acoustic waves, then the semiconductor substrate having semiconductor devices formed thereon may be reworked, modified or scrapped. In each case, the remaining or resulting semiconductor devices will function at a more reliable level and the yield of the process may be higher, thereby resulting in higher profits for a chip manufacturer. Two processes that may be monitored using the analysis of surface acoustic waves are deposition processes and chemical mechanical planarization processes. Analysis of surface acoustic waves may be applicable to other semiconductor and biologic manufacturing processes as well.

DETAILED DESCRIPTION

In the following detailed description of the invention, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims and equivalents thereof.

A simple, exemplary method for analyzing surface acoustic waves as a means for obtaining information about the structure or mass loading of a substrate is to induce surface acoustic waves at a first point and measure their time of arrival at a second point that is spaced a known distance apart from the first point. This technique involves the arrangement of optical elements and/or gratings/masks to ensure that the surface acoustic waves are induced and analyzed at desirable locations. In another embodiment, plasmonic optical elements and/or metamaterials may be used to induce surface waves at finer resolutions than standard diffraction of light would otherwise permit. This can be done in the near field and also in the far field.

Multiple gratings, apertures, and devices various dimensions and pitch may be used to measure the dependence of surface acoustic wave frequency vs. lateral wavelength—e.g. the acoustic dispersion—and this information may be used to decouple multiple parameters in the substrate—e.g. film thickness from the film's elastic properties, or film thickness from the substrate's elastic properties. One benefit of using an array of slits or apertures is that the array may be formed to have a variable pitch over its extent to assist in decoupling the aforementioned parameters. Additional parameters may also be obtained, e.g. stress of the material forming the substrate. Additional parameters may, in the future, be identified and decoupled using the approaches set forth in this application and the claims appended hereto are not to be limited to only those parameters listed.

Figure 1:
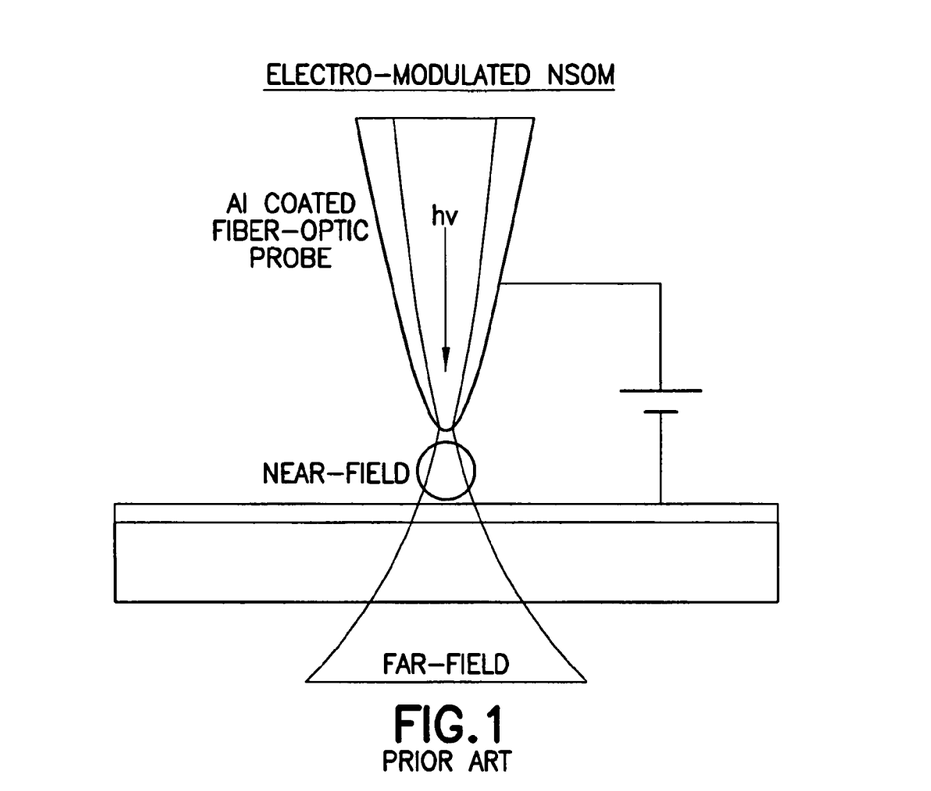
FIG. 1 is a schematic side view of a prior art NSOM device.

A metrology system 5 for obtaining information such as dimensions or other characteristics of a homogenous or structured substrate may involve the use of a number of near-field scanning optical microscopy (NSOM) devices as pump and probe illumination and collection elements. A schematic drawing of a typical prior art NSOM device that may be used as either a pump or a probe element in a surface acoustic wave metrology system is shown in FIG. 1. The NSOM illustrated in FIG. 1 has a small aperture defined by the coating on the optical fiber probe though it is to be understood that non-apertured NSOM's may also be used. Note that in an NSOM, light is generally transmitted to/through the NSOM using an optical fiber. Similarly, light may be returned from an NSOM by an optical fiber.

Figure 2A:
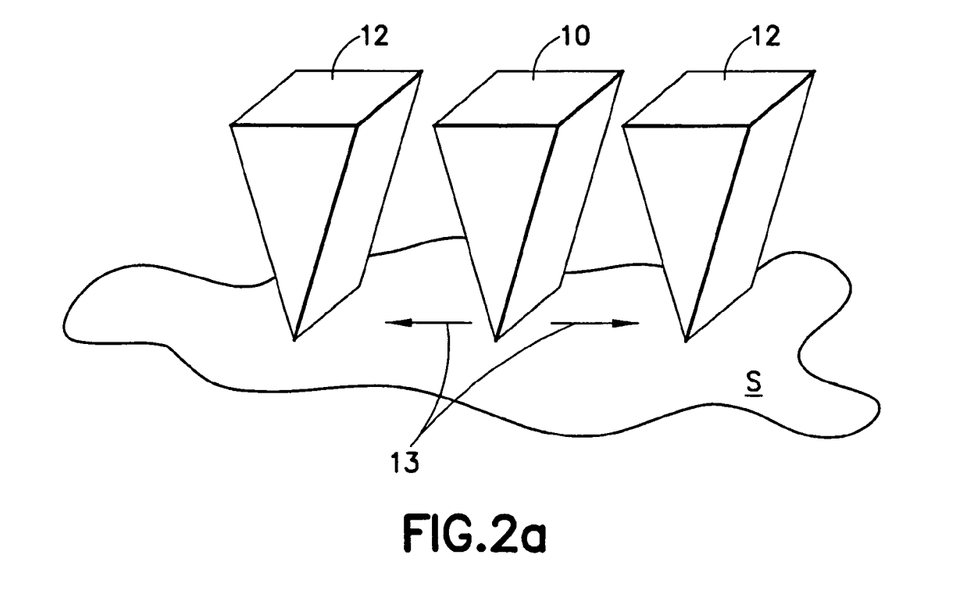
FIG. 2a is a schematic closeup of one embodiment of NSOM derived pump and probe elements of a surface acoustic wave analysis system.

In one embodiment, a partial schematic of which is illustrated in FIG. 2a, a first NSOM is used as a pump element 10 to induce a surface acoustic wave (arrows) in a substrate S. One or more additional NSOM's are used as probe elements 12 to sense the presence of acoustic surface waves (arrows 13) in the surface of the substrate S. Note that in contrast to the NSOM shown in FIG. 1, the NSOM's shown in FIG. 2 are elongate, having a generally prismatic shape, though in practice the shape may vary so long as the function is maintained. Specifically, the NSOM's shown in FIG. 2 include a linear aperture or output end.

The NSOM pump and probe devices 10, 12 of the embodiment shown in FIG. 2 are constructed to illuminate the substrate S and/or to receive light from the substrate S in a shape that is elongated and generally linear in shape, e.g. a narrow slit. In some embodiments, the slits may have a width of 50 nm, a length of 5 microns and a pitch of 100 nm and be generally parallel with one another. A benefit of the slit version of the NSOM device is that a surface wave induced in the substrate S has a larger wavefront propagating in the direction of the probe devices 12 than is the case for a surface acoustic wave propagating from a first NSOM defined by a small spot toward another NSOM defined by a small spot that is used as a probe. Accordingly, an effect of surface acoustic waves on the light incident on and/or reflected from the substrate at the probe devices 12 is proportionately greater than it would be for a small spot NSOM probe device.

In operation a pump pulse of light may be directed by the pump element 10 onto the surface of a substrate S under test. The incident light may be of any useful wavelength or combination of wavelengths, e.g. it may be substantially monochromatic or may exhibit a range of wavelengths, i.e. essentially white light. Further, the light may be polarized at any suitable angle or shape (e.g. circular or elliptical) or may be essentially unpolarized, as required by the application in question. The incident pulse of light rapidly heats the surface of the substrate which expands at a rate that creates the aforementioned surface acoustic wave. The surface acoustic wave is a travelling perturbation in the surface of the substrate S. The surface acoustic wave induces a transitory change in the reflectance of the substrate as it passes through the substrate. Further, light reflected from a substrate may be scattered or the specular reflection of light may be deflected by the physical deformation of the substrate due to the passage of the surface acoustic wave.

Pump pulses of light may be of short duration and high amplitude and when an NSOM pump device 10 such as that shown in FIG. 2 is used, the pump pulses of light may be incident at near normal angles. Note that NSOM devices are generally intended to be positioned very close to the substrate that is under test such that diffraction is not sufficient to cause a high degree of dispersion of the pump pulse of light emitted from the NSOM device. Accordingly, for both the NSOM pump and probe elements 10, 12, the spot size of the pump and probe pulses of light are similar to the dimensions of the outlet of the NSOM devices themselves. Accordingly, to some degree one may define a resolution of a surface acoustic wave metrology system by controlling the dimension of the pump and probe elements themselves. Pump pulses of light may be incident on the surface at a periodic rate of about 50 MHz. This rate may be constant in that the rate of 50 MHz may remain substantially the same over time or may be varied in a continuous or discontinuous way depending on the needs of the application.

In one embodiment probe pulses of light are directed from a light source 15 (FIG. 2b) through the probe element 10 onto the surface of the substrate S. As the surface wave induced by the pump pulse of light passes through the location where a probe pulse of light is incident, the reflectance of light is modified and/or scattering or deflection of light modify the intensity of the light reflected from the substrate that is collected by a separate lens. Note that the wave front of the surface acoustic wave created by a linear NSOM pump device 10 is essentially linear where it intersects the NSOM probe devices 12. One will appreciate that the surface acoustic wave will propagate in a direction substantially normal to the edges of the area where the substrate S is heated by the pump pulse of light.

Figure 2B:
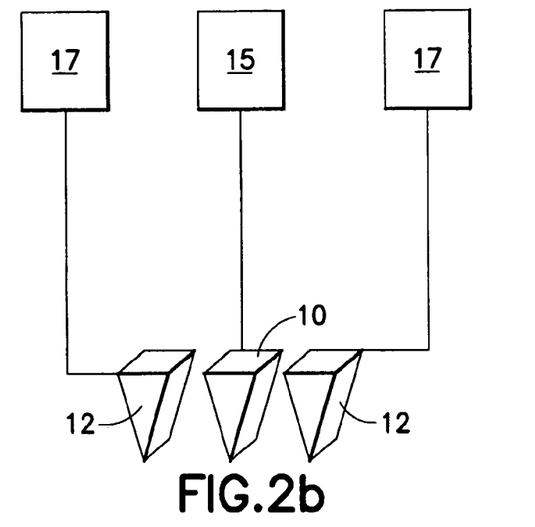
FIG. 2b is a partial block diagram of an embodiment of a surface acoustic wave analysis system.

Probe pulses of light may be focused through a probe element 12 onto the surface of the substrate S beneath the probe element 12. As the surface wave induced by the pump pulse of light passes through the location beneath the probe devices, the reflectance of light is modified and/or a scattering or a deflection of light modifies the intensity of the light reflected from the substrate that is collected by the NSOM probe elements 12.

Light received from a substrate S through NSOM is directed to one or more sensors 17 which record its intensity. This intensity may be measured as a function of delay time between pump and probe pulse trains, as the frequency of a surface acoustic wave provides insight into the mass loading and mechanical properties of the substrate. Similarly, the intensity and other characteristics of light returned from the substrate S may be measured. For example, the polarization state of light, wavelength, phase, and other optical characteristics may be obtained.

Figure 2C:
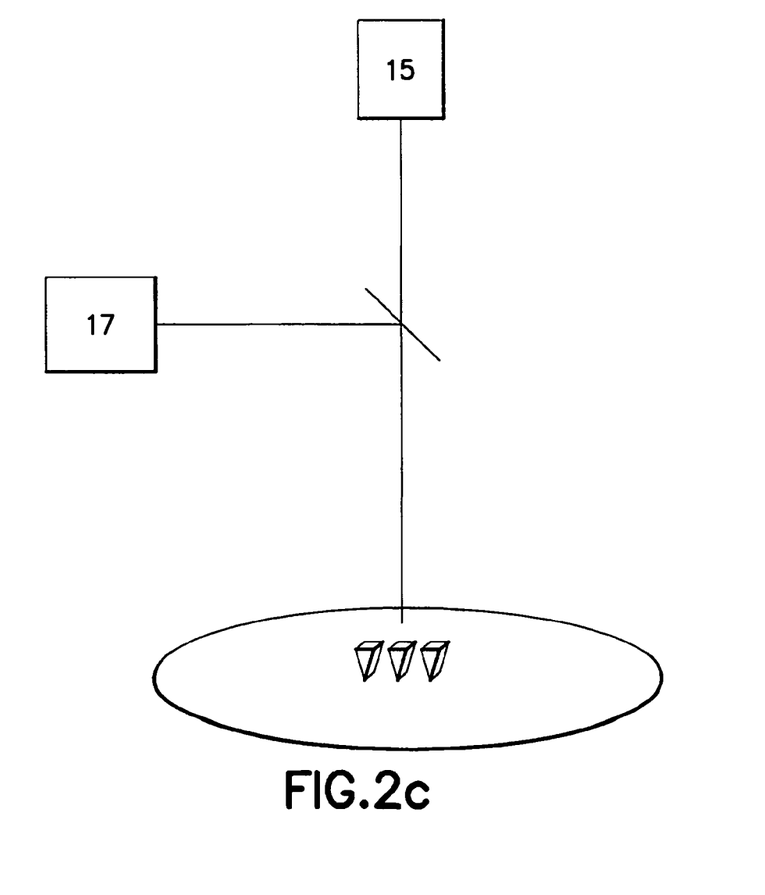
FIG. 2c is a partial block diagram of an embodiment of a surface acoustic wave analysis system.

While the system 5 as shown in FIG. 2b has separate illumination and sensing connections between the NSOM devices used as pump and probe element and an illumination source and sensors, it is also possible that a single optical connection may be made to the pump and probe elements 10, 12 shown in FIG. 2c. As shown in the embodiment of FIG. 2c, only a single illumination source 15 and sensor 17 are required.

As will be appreciated by those skilled in the art, illumination source 15 and sensors 17 may be provided with standard optical elements typically associated with optical sensing techniques such as polarizers/analyzers, filters, modulators (e.g. acousto-optic or electro-optic modulators) and the like. These optical elements, as well as others known to those skilled in the art, may be used to direct light to and from the NSOM devices and may also be used to condition, focus, mix or otherwise modify the characteristics of the incident or reflected light moving through the system 5 in such a manner as to obtain useful data. Further, suitable light sources may be selected from any of a range of such items and may include lasers, light emitting diodes (LED's), incandescent light sources, and the like. These light sources may output any suitable wavelength at any suitable power. Similarly, suitable sensors for obtaining data concerning a substrate from the light returned from the substrate may include any suitable type of photodetector sensitive to wavelengths identified as being returned from the substrate when the substrate is under test. Suitable sensors may include charge-coupled devices (CCD), photomultipler tubes (PMT), and the like.

Mass loading refers to the cumulative effect of structural features, sizes, and material characteristics that affects how acoustic waves travel through the substrate. For example, where a substrate having multiple layers of materials of different materials is analyzed, a thickness of one or more layers deposited on a substrate S that is under test will affect the way acoustic waves travel through the substrate. The thicker a layer or stack of layers, the lower the frequency of the surface acoustic wave will be and vice versa. In addition, the elastic properties of the materials in the substrate may affect the surface wave frequency. The measured characteristics of light (such as intensity) may be converted into the desired metrology data (e.g. layer thickness) by means of a calibration process, but the substrate and its one or more layers may also be mathematically or empirically modeled. In this latter case, a conversion between measured intensity and the desired metrology data is obtained by looking up corresponding values in a table, by interpolating or extrapolating between or from modeled values, or by solving the one or more equations of a model that can directly convert between the measured intensity of light and the desired metrology data. Note that it may be the case that a model may have too many degrees of freedom to solve directly. Accordingly, in one exemplary embodiment, regression techniques may be used to determine the desired metrology data and/or to generate the data used to populate a look-up table or from which inter/extrapolation may be performed.

In some embodiments a substrate S will have discontinuous structures formed within its volume or in or on the surface thereof. Discontinuous structures such as electrically conductive traces, inclusions, air bubbles and the like also affect the mass loading of a substrate and may be similarly modeled and/or measured.

Probe pulses of light returned from the substrate may be measured as the function of any of a number of additional inputs as well, including without limitation the polarization state of the probe pulse of light and the wavelength. Additional variables may be used as those skilled in the art progress in the design of suitable sensors, illumination systems, and numerical and empirical methods of converting sensor data into metrology data.

While it is conceptually possible for a probe beam of light to be continuously incident on a substrate subject to the imposition of surface acoustic waves, it may be difficult for a sensor to operate fast enough to keep up. For example, if the physical arrangement of the pump and probe NSOM devices 10 and 12 and the acoustic properties of the substrate under test are such that the propagation of the surface acoustic wave will propagate from its initial position adjacent the pump device 10 to a subsequent position adjacent the probe devices 12 at rate that approaches or exceeds the rate at which the sensor can sample data, then the measured results may be too coarse to be of use or the effect that is to be measured may be missed entirely. Accordingly, until such time as sensors are fast enough to provide repeatable resolution at rates suitable to the speed at which the surface acoustic waves propagate through the substrate under test, it may be preferable to use an optical sampling (pump/probe) technique which is capable of achieving sub-picosecond time resolution.

One example of such a pump probe system is found in U.S. Pat. No. 6,400,449, which is incorporated by reference herein in its entirety. Tracking the propagation of surface acoustic waves between the pump device 10 and the probe devices 12 is accomplished in a manner that is similar to sonar and which is described more fully in the aforementioned '449 patent. In brief, a short pump pulse of light having a predetermined wavelength and intensity is applied by means of the pump element 10 to a predetermined position on the substrate S under test for a predetermined duration. Appropriate selection of power and duration of the probe pulse, as well as the selection of some additional characteristic such as wavelength or polarization state, allows the probe pulse of light to be efficiently coupled to the surface of the substrate S, thereby heating the surface of the substrate fast enough to create an acoustic wave that travels along the surface of the substrate. Simultaneously or immediately thereafter, probe pulses of light having a known wavelength and intensity are applied by means of one or more probe elements 12 to one or more predetermined positions on the surface of the substrate S under test. The probe pulses of light are used to measure changes in reflectivity or in the shape of the surface on which the probe pulse of light it is incident, such changes and the time at which they are recorded with respect to pump pulses of light being indicative of certain characteristics of the substrate that is under test. Note that the characteristics sensed by the probe elements 12 are transitory in nature but may be correlated with geometric, material and structural properties of the substrate S, i.e. they may provide information about the mass loading of the substrate.

Pump and probe pulses of light are serially directed to the substrate with a selected time delay therebetween. In one embodiment, a pump/probe sequence is repeated a sufficient number of times at a selected time delay setting to allow the signal to be integrated over a period of time, thereby increasing the signal to noise ratio. Thereafter, the time delay between when the pump and probe pulses of light are applied through the pump and probe elements 10, 12 is modified. In some cases, a time delay element may be interposed into an optical path to change the time delay. This pump/probe sequence is also carried out a sufficient number of times to ensure that the signal is properly integrated over time. While it is conceptually possible to obtain sufficient useful information from a single pump/probe sequence, current sensor technology makes this difficult. Improvements in sensor technology may allow for the reduction in the amount of integration required to obtain practical results and such improvements are intended to be incorporated into the broad concept disclosed herein.

A time delay element may be mechanical or optical or a combination of the two. In use, the pump/probe pulses of light are directed to the surface of the substrate at a high repetition rate and that accordingly, the time delay stage or other mechanism or method of beam shaping or of modifying the time delay, can vary the time delay continuously. In one embodiment, an opto-mechanical time delay in which a mechanical stage lengthens or shortens the beam path of the probe pulse of light is operated to continuously or discontinuously modify the time delay. It is possible to change the time delay for each successive iteration of pump and probe pulses of light. In another embodiment the geometry of a resonant cavity of a laser source is modified to change the repetition rate of the resulting laser. This modification can be achieved by coupling a mirror in the resonant cavity to an actuator, e.g. a piezoelectric actuator, that can change the optical path length of the cavity. This device is referred to as an asynchronous optical sampling (ASOPS) device.

The time delay between the imposition of the pump beam of light and the time at which data is collected by a probe element is chosen based on a desired time of flight of the acoustic wave that is of interest to the user of a system 5. For example, if a model of a substrate S indicates that for a given substrate mass loading a nominal time of flight for a surface acoustic wave is 1 ms, a series of time delays will be selected both above and below the nominal time of flight. In this way, variations in the mass loading of the substrate S may be identified. Note that this example may or may not be indicative of a true time of flight in a given substrate and accordingly, this invention is not limited to time delay values in this range.

As indicated above, a time delay may be modified continuously. In one embodiment, a single time delay between the pump and probe pulses of light applied to the substrate is set and a predetermined number of pump/probe pulses of light are applied to the substrate S to generate a predetermined number of data. The predetermined number of data obtained at a given time delay setting may then be integrated, averaged or otherwise modified or stored in an unmodified form for later processing. Subsequently, a second time delay setting may be selected and a subsequent set of data obtained. This process continues until all desired time delay settings have been addressed. This process may proceed slowly as where the time delay is manually modified or very quickly as where the time delay is managed by a solid state device such as an ASOPS.

Alternatively, the time delay may be continuously modified and data obtained at selected time delays. Cycling the time delay multiple times will allow a sensor to obtain data at different time delays. Note that data may be obtained at a rate of one or more reading per cycle of the time delay element. The rate at which data may be obtained is limited by how fast the pump/probe pulses of light may be applied to the substrate, how fast the sensor may obtain data and how fast the time delay element cycles through a selected range of time delays.

Generally the system 5 will remain stationary at a selected portion of a substrate S to obtain data about that location. However it is possible that where data recordation, the modification of the time delay and the application of the pump/probe pulses of light can be cycled fast enough, data that is indicative of the mass loading of a substrate may be obtained while the system 5 moves relative to the substrate. This may be particularly helpful where a substrate S has a selected area that has a structure that is essentially homogeneous, e.g. single layers or multiple layers that extend beyond the area that effects the readings of the system 5.

Note that while a single pump element 10 and two flanking probe elements 12 are shown in FIGS. 2a-c, it is contemplated that any useful number of such elements may be provided. For example, multiple sets of devices 10, 12 such as those shown in FIGS. 2a-c may be formed into an array or pattern suitable for the measurement of substrate characteristics.

Figure 3:
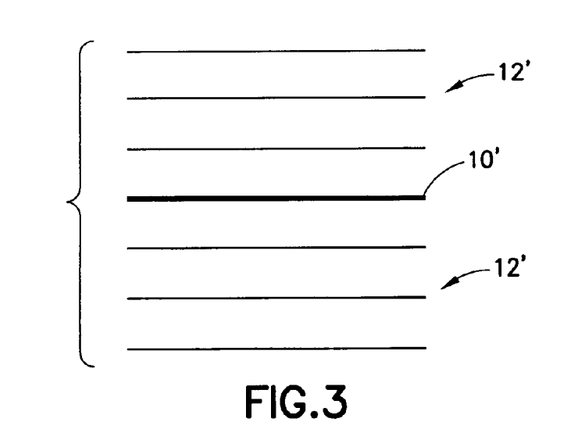
FIG. 3 is a schematic representation of a pattern of light or radiation formed on a substrate by an embodiment of a surface acoustic wave analysis system.

In one embodiment, shown in FIG. 3, a single elongated slit 10' that is established by pump element 10 is flanked on either side by a plurality of slits 12' established by probe devices 12 (e.g. more than one on each side). In this way, a surface acoustic wave may be analyzed at substantially a single lateral wavelength or k-vector to minimize measurement uncertainty resulting from dispersion (e.g. surface acoustic wave velocity dependence on wavelength). An increase in signal level and precision may further be gained by using an array of pump slits 10' that are overlapped with probe slits 12' and also having the same period as the probe slits 12'. Several pump/probe slit periods may be measured sequentially or simultaneously to measure the surface acoustic dispersion and to calculate multiple parameters of the substrate S. The shape and size of the respective slits may also vary. By way of example, in some instances the slits may be linear and of any useful length. In other embodiments, the pump slits may be a curvilinear shape or a rectilinear shape. In various embodiments, the probe elements 12 may be positioned and sized such that a selected surface acoustic wave intersects substantially the entire probe slit 12' at substantially the same time. The respective probe elements may be formed into rectilinear radial arrays or arrays of arrays. Further, it may be desirable, though not strictly necessary to form and position each of the probe elements 12 in a parallel fashion as shown in FIG. 3. In other embodiments, probe devices 12 may be formed circumjacent to a pump element 10 in a bullseye fashion with each ring being substantially concentric to the other(s). In embodiments where the substrate S is provided with an asymmetric feature or structure, it may be desirable to fashion a similarly asymmetric array or arrangement of the elements 10, 12, though the modeling used to convert measured data into metrology data may accommodate such differences.

While it is not necessary to form the probe elements 12 in a strictly regular pattern with respect to one another and/or to the pump element(s) 10 with which they are associated, one benefit of symmetry is that surface acoustic waves propagating symmetrically outward from the location in which they are formed may intersect the probe elements 12 at predictable times. Further, symmetry of the arrangement of probe elements 12 with respect to one another and with respect to one or more pump elements 10 may permit constructive interference as where a single surface acoustic wave intersects symmetrically positioned probe elements 12 to simultaneously to boost the magnitude of a resulting signal. Where fabrication issues or defects affect the pump and probe elements, unintended asymmetry may be calibrated and modified or removed when the measured data is processed into metrology data.

In another embodiment in accordance with the present invention, an NSOM element may be replaced by what is referred to herein as a nanolight element. The term "nanolight" is not necessarily a term of art, but as used herein refers to a device for reducing diffraction in an optical system using one or a combination of plasmonic coupling structures, metamaterials and/or constructive interference optical elements or techniques. Nanolight elements or structures may, but do not necessarily exhibit decreased diffraction of light (depending on the arrangement) and/or negative indices of refraction.

Figure 4:
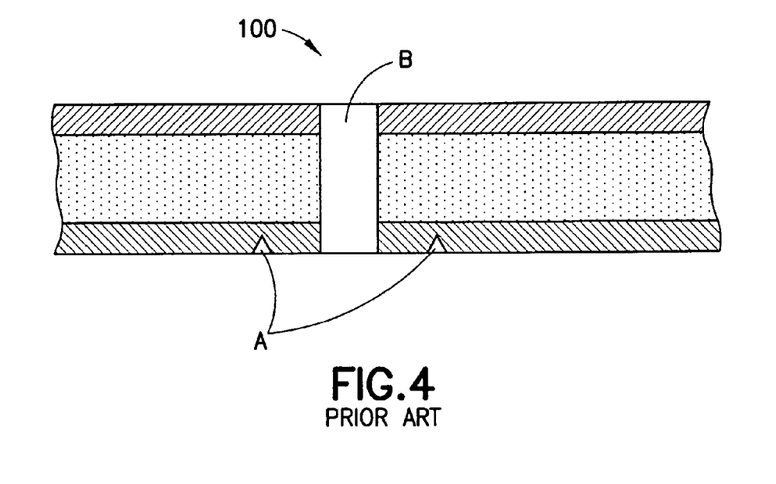
FIG. 4 is a schematic cross-section view of one aperture of a prior art nanolight element.

One example of a prior art nanolight element 100 as described by Stark et al. in U.S. Pat. No. 6,818,907, incorporated by reference herein in its entirety, is seen in FIG. 4. Nanolight element 100 comprises one or more small holes or narrow lines B milled through and/or into a metal film or stack structure. The repeat distance of the holes, lines, and/or augmentation features A is designed to match energy and momentum of the incoming photons to the metal film's surface plasmons thereby resulting in an antenna with transmission coefficients greater than unity. Furthermore, the asymmetric nature of the structure (e.g. air/metal/substrate) can result in a directed beam exiting the opposite surface. The resulting beam is capable of illuminating holes or lines having a width of 30 nm that are spaced 150 nm apart. When a ray or beam from a nanolight element 100 is reflected from a substrate, that beam or ray is passed to standard refractive or reflective optical elements or optical fiber elements and ultimately to a sensor such as a CCD, CMOS or similarly useful photodetector/sensor adapted for capturing an image or some characteristic of light. Other devices and techniques that can be classified as nanolight elements are known to those skilled in the art. One embodiment of an optical system for measuring layer thickness or other characteristics of a substrate that takes advantage of nanolight element technologies is shown in FIGS. 5a and 5b.

Figure 5A:
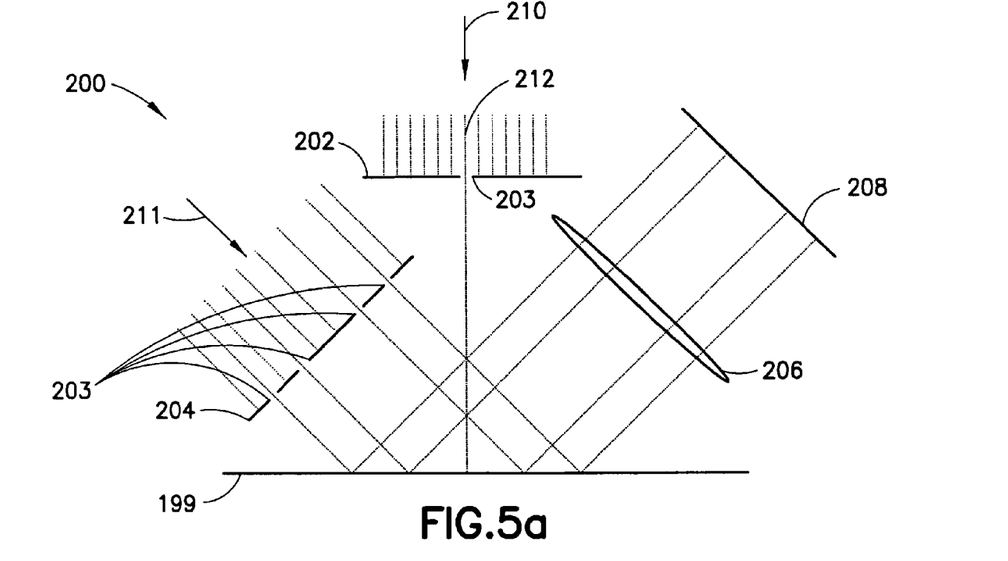
FIG. 5a is a schematic representation of an embodiment of nanolight derived pump and probe elements a surface acoustic wave analysis system in which pump and probe beams of light are separated from one another.
Figure 5B:
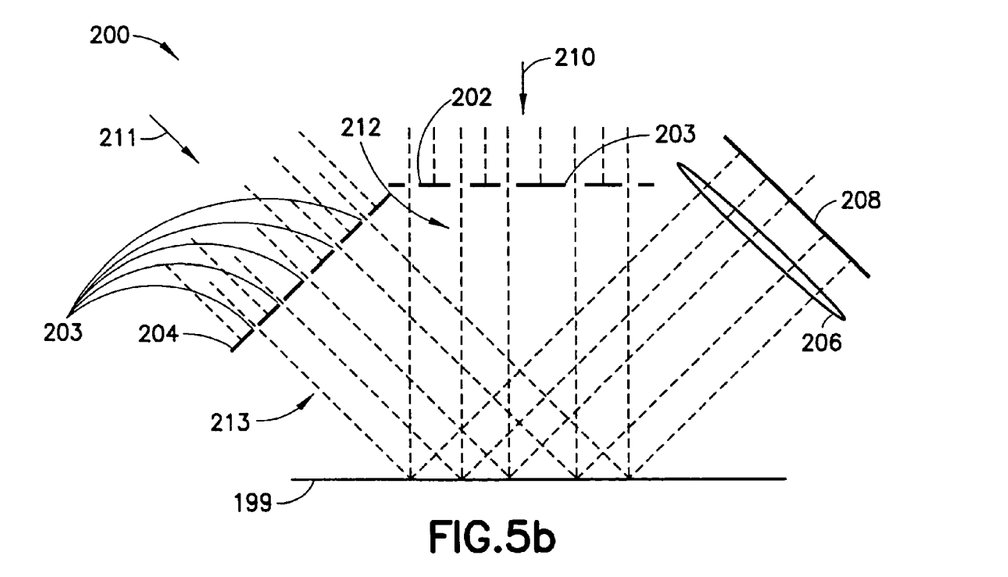
FIG. 5b is a schematic representation of an embodiment of nanolight derived pump and probe elements a surface acoustic wave analysis system in which pump and probe beams of light are coincident with one another.

FIG. 5a illustrates an optical sensor package 200 that includes a pump element 202, a probe element 204, collection optics 206, and a sensor 208. Additional components such as computers or processors for operating a metrology system 5 based on the package 200, automation components such as wafer or substrate handlers or top plates, and illumination sources are not shown for in FIG. 5 for the sake of clarity. Those skilled in the art will readily understand how and where these types of components should be included and operated.

Coherent or incoherent light (represented by arrow 210) of any selected wavelengths or selected ranges of wavelengths is incident upon the pump element 202 at an angle of incidence selected to maximize transmittance of light through a bore or slit which will hereinafter be referred to as an aperture 203. Note that while FIG. 5a appears to show that light is incident on the pump element 202 at near normal incidence, other angles of incidence may be used. Further, the pump element 202 may be arranged at any useful azimuthal, pitch or roll angle with respect to the substrate 199. Light 210 may be provided from any of a number of commercially available coherent or incoherent light sources and along open air paths or through light guides or optical fibers and may also be polarized to any extent or angular orientation required by the application at hand. As the efficiency of a nanolight device is, at least in part, depending upon a function of angle of incidence, wavelength, polarization, and aperture structure, acceptable performance may be obtained from many different combinations of pump/probe nanolight elements and associated optical elements and setups.

Photons of light 210 are coupled into surface plasmons or plasmonic waves on the surface of the pump element 202. The surface plasmons augment the amount of light 210 that passes through the aperture 203 to form beam 212 that is incident on the substrate or film stack 199. The amount of light that passes through aperture 203 to form beam 212 is such that the absolute transmission efficiency of light through the aperture 203 of pump element 202 is approximately ≥1, though it is possible that lesser or greater transmission efficiencies may be achieved.

As described above, the diffraction experienced by beam 212 may be less than would otherwise be expected, e.g. for any given wavelength, the diffraction experienced by the light passed or emitted by the beams 212 may be less than the diffraction predicted by the equation $$d = \frac{\lambda}{2n\sin\alpha}.$$

Beam 212 is incident on the substrate 199 so as to induce acoustic waves in the surface of the substrate 199 that propagate outwardly as described above in conjunction with FIGS. 2 and 3.

Light 211 is incident on probe element 204 at a predetermined time delay with respect to the probe pulse of light 212. Light 211 passes through apertures 203, which may be cylindrical bores, elongate slits, or any other useful shape. Note that as with light 210, light 211 is incident upon the nanolight probe element 204 at any useful angle of incidence and/or polarization state and probe element 204 itself may be positioned at any useful azimuthal, pitch or roll angle. Further, light 211 may be monochromatic or polychromatic and coherent or incoherent.

As light 211 is incident upon probe element 204, a portion of the light 211 passes through the apertures 203 to form beams 214. Note that the probe element 204 is adapted to couple the incident light 211 into surface plasmons or plasmonic waves such that the absolute transmission efficiency of light through the apertures 203 of probe element 204 is approximately ≥1, though it is possible that lesser or greater transmission efficiencies may be achieved.

FIG. 5b illustrates an alternative to the embodiment of FIG. 5a in which multiple apertures or slits 203 are arranged to direct multiple beams 212 of light onto substrate 199. Note that the locations at which beams or rays of light 212 and beams 213 are incident upon the substrate 199 are in substantially the same locations.

Where the apertures 203 of probe element 204 of the optical sensor package 200 are formed as cylindrical bores, it may be desirable to form an array of probe element apertures 203 around or adjacent to the pump element apertures 203. Note that in some instances, the apertures can do double duty as both pump and probe element apertures as where the pump and probe beams of light are incident on a single element that imposes the desired pinhole or slit pattern or array.

Figure 6A:
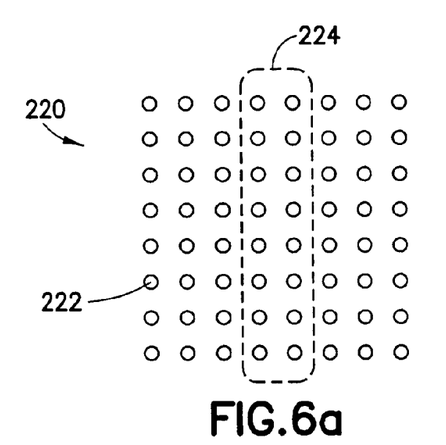
FIGS. 6a-6d are schematic representations of various embodiments of nanolight elements.

As can be seen from FIGS. 5a and 5b and also FIG. 3, probe beams may be incident upon a substrate 199 in multiple locations. FIGS. 6a-d shows a number of additional possible arrangements of pump and probe locations upon a substrate. In FIG. 6a an array 220 of apertures 222 may be used as a nanolight element, with apertures 224 within the dashed line being designated as the pump beam apertures. Light incident on the multiple apertures 224 may be provided by any suitable means such as fibers positioned to emit light only on the selected apertures and/or the incident light may be limited by another mask, aperture, or slit (not shown) to segregate pump light from probe light. But, in some instances it may be acceptable to have pump and probe light incident upon all apertures 222 of the array so long as the sensors capturing data are able to distinguish the resulting signals.

Figure 6B:
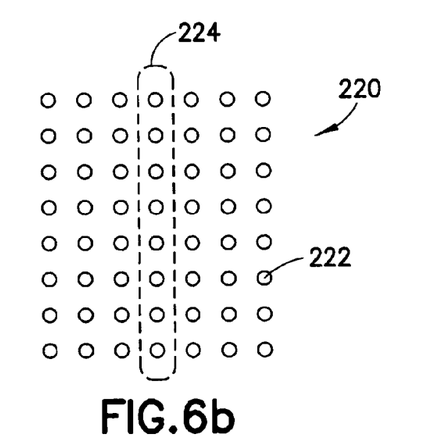

FIG. 6b shows a similar arrangement to that shown in FIG. 6a, a difference being that fewer apertures 222 are selected for use as probe beam apertures 224. Note that neither of FIGS. 6a and 6b are definitive in terms of how apertures may be arranged, but rather these Figures are mere exemplars of the many different ways in which apertures may be arranged for the measurement of surface acoustic waves as described above.

Figure 6C:
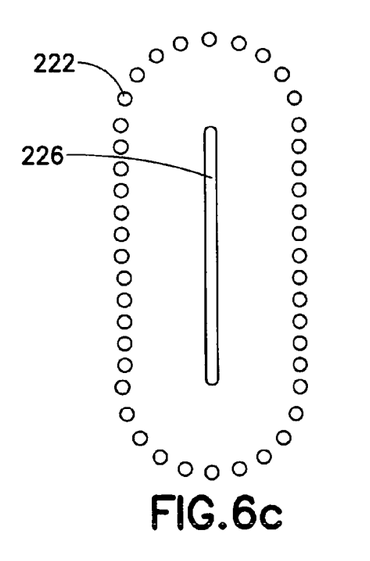
Figure 6D:
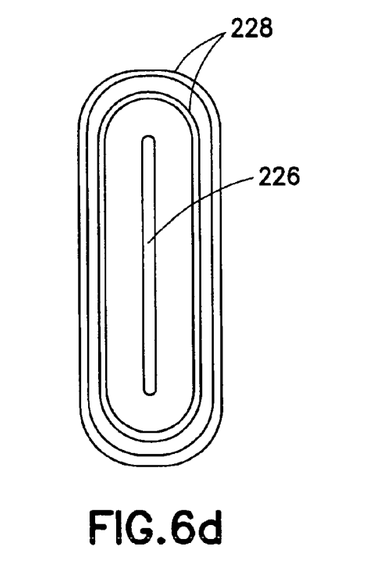

FIG. 6c shows multiple apertures 222 positioned about a slit 226 used as a probe beam aperture. FIG. 6d shows multiple rings 228 of slits (shown schematically) formed about a single slit 226 that is used as a probe beam aperture. Again, these arrangements may be modified to obtain a more optimal signal.

It should also be kept in mind that each of the apertures and slits shown in the Figures that accompany this text are schematic in nature. In order to obtain the desired transmission efficiency and/or to limit diffraction, each aperture or slit may have additional structures formed therein or therearound in the upper and/or lower surfaces thereof. In one embodiment, each aperture and slit has at least one annular groove formed in the upper surface thereof wherein light is incident upon both the aperture or slit and the surface of the element having the annular groove formed therein. This type of structure may assist in improving the transmission efficiency of the nanolight element by increasing the number of photons that are coupled into the nanolight element as plasmonic waves.

Figure 7:
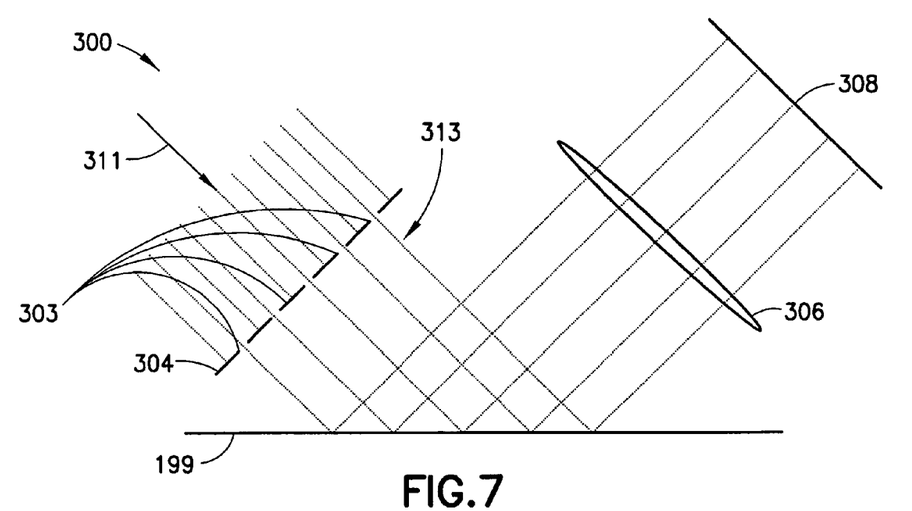
FIG. 7 is a schematic representation of an embodiment of nanolight derived pump and probe element together with collection optics of a surface acoustic wave analysis system.

FIG. 7 illustrates another exemplary embodiment in accordance with the present invention in which a single element 304 defines a light pattern on the surface of a substrate 199.

Light 311 is incident upon the element 304 which has a number of apertures 303 formed therethrough. The apertures 303 define beams or rays 313 that are incident upon the substrate 199 to form the desired pattern. As described above, the apertures 303 may take any useful shape, but are in some instances cylindrical bores formed through the element 304 or elongate slits. The apertures 303 may be included in any useful number. Examples of some arrangements of apertures 303 are shown in FIGS. 6a-d. Note that element 304, as well as elements 204 and 203 in FIGS. 5a and 5b, may be simple plated mask structures such as a grating or, as described below, a nanolight device or element.

In some embodiments, the element 304 may be a nanolight device that takes advantage of plasmonic wave coupling, metamaterial construction and/or the use of constructive interference to obtain the desired optical arrangement. For the purposes of this application, a metamaterial is any material that obtains its electromagnetic properties from its structure rather than from its chemical composition; especially a material engineered to have features of a size less than that of the wavelength of a class of electromagnetic radiation. In one embodiment, light 311 is incident on element 304 in a manner that allows for the incident light to form highly collimated beams that pass through apertures 303. Note that because of plasmonic coupling, the structure of the element 304, and/or constructive interference, the beams that pass through or which are emitted from element 304 are subject to reduced diffraction and enjoy a greater transmission efficiency than might conventionally be expected.

In operation a pump beam of light is incident upon the element 304, which emits and/or passes the pump beam of light to the substrate 199 that may be a film stack. The pump beam of light induces a surface acoustic wave in the substrate 199 by means of thermal coupling of the pump beam of light into the surface of the substrate 199. The surface acoustic waves then travel outwardly from the locations at which they were induced. Note that because the apertures 303 form an array of spots or slits on the substrate 199, the surface waves will propagate from those spots or slits towards the other spots or slits formed by the apertures 303 of element 304.

As described above, a subsequent probe beam of light 311 is then incident on the element 304. Note that the probe and pump beams of light may be collinear with one another as where the separate beams have been joined by means of an element such as a beam splitter or may be coincident with one another as where two or more separate beams are directed to be incident upon the same element 304. The probe beam of light 311 is, like the pump beam of light, passed and/or emitted by the element 304 as a number of beams that form substantially the same pattern of spots or slits as was formed by the pump beam of light. The probe beams of light incident upon the substrate 199 are incident at a selected time delay with respect to the pump beam of light such that variations in the probe beam of light detected at the selected time delay are indicative of certain characteristics of the substrate 199, including film thickness, index of refraction and the stress present in the substrate 199 itself. In short, while it may be possible to spatially segregate the pump beams of light from probe beams of light on a substrate 199 under test, it is not necessary so long as an acoustic surface wave may travel from a point at which it is induced by a pump beam of light to a point at which it may be monitored by a probe beam of light. In some embodiments this may involve two spatially separated points, each one being addressed by only one of the pump and probe beams of light and in other embodiments this may take the form of an array of points or slits that are all addressed by both the pump and probe beams of light.

When a single nanolight element is used for both pump and probe beams the reflected pump and probe beams may be coaxial and it may be desirable to separate the pump and probe beams of light prior to detection in order to achieve an acceptable signal to noise. To achieve this, one method is to utilize pump and probe beams of light that are in distinct polarization states with respect to one another. In one embodiment, light from a first light source intended for use as a pump beam of light is polarized to a selected polarization state and light from a second light source is polarized to a selected polarization state that is distinct from that of the first light source. An analyzer (not shown) positioned between or within the collection optics 206, 306 may be positioned to prevent the passage of light from the pump beam to the sensor 208, 308. Note that where a nanolight element or a grating are used, it is possible to select a polarization state that is consistent with the desired operation of the selected nanolight or grating element.

In another embodiment, the wavelengths of the pump and probe beams of light are distinct from one another and a wavelength specific filter or filters can be included in the collection optics 206, 306 to prevent the pump beam of light from being incident on the sensor 208, 308.

Figure 8:
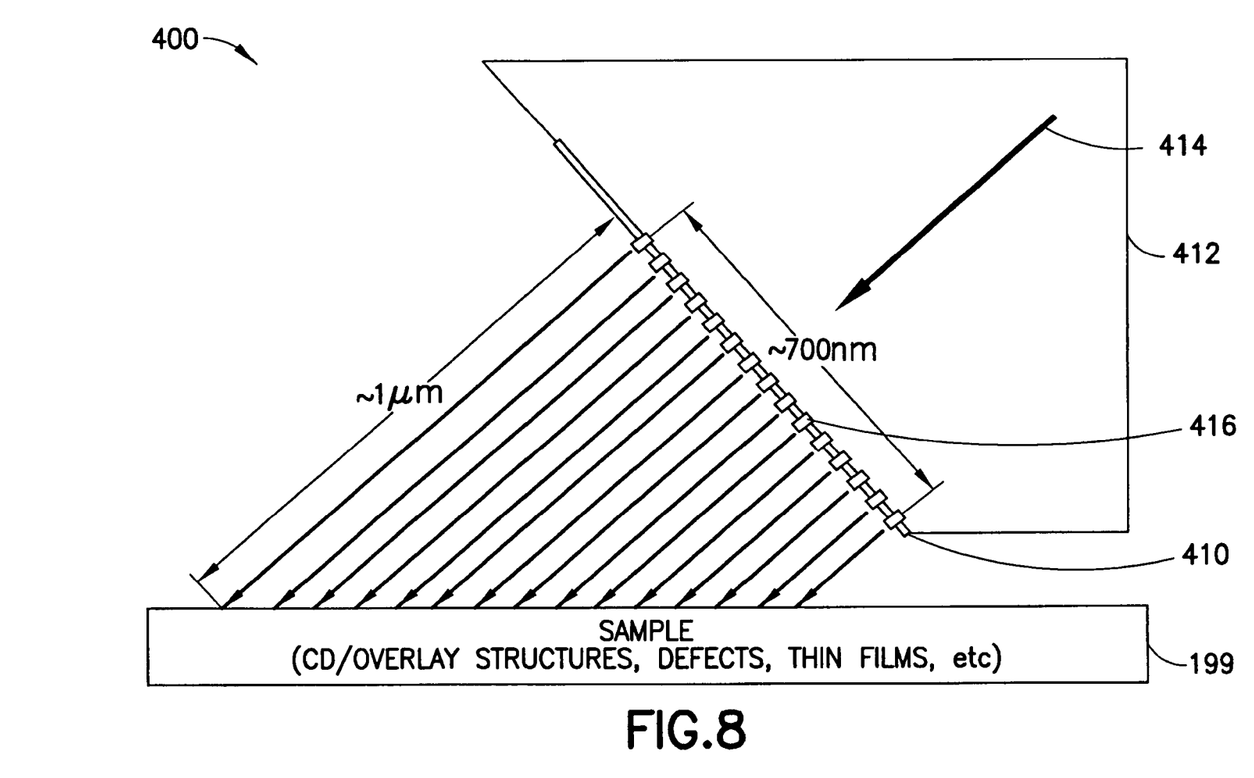
FIG. 8 is a schematic representation of an embodiment of nanolight derived pump and probe elements mounted on a solid optical element.

FIG. 8 illustrates an exemplary embodiment of an optical system 400 that incorporates an example of a nanolight element 410 that is formed onto a flat side of a solid optical element 412. The optical element 412 may be an output end of an optical arrangement, e.g. an optical fiber system, a light guide, or a selected set of refractive and/or reflective optics, that conducts light from a light source (not shown) to the sample 199. Light emitted from optical element 412 and/or directed onto nanolight element 410 may be collimated or directed light, and may conditioned so as to achieve a sufficient (or minimum) coupling efficiency of photons to plasmonic waves in the surface.

As described above, the light source (not shown) may be any suitable source of coherent or incoherent light and may be monochromatic or polychromatic. Further, optical elements (not shown) such as lenses, reflectors, beam splitters, polarizers, quarter wave plates, and/or filters of any useful soft (e.g. wavelength specific or spatial) may be included in the optical path between the light source (not shown) and the solid optical element 412. Arrow 414 represents light from the light source that is incident upon the nanolight element 410.

In the embodiment illustrated in FIG. 8, the nanolight array 410 is provided with a series of apertures 416. These apertures 416 may be cylindrical bores or elongate slits of any suitable size or range of sizes and may be positioned in a uniform array or in any other suitable or useful spatial orientation. In the embodiment shown in FIG. 8, the nanolight element 410 has a lateral extent in one direction of approximately 700 nm. It is to be understood that this dimension is exemplary and that the nanolight element 410 may be of any useful size. The distance between the nanolight element 410 and the sample 199 is in the embodiment of FIG. 8 approximately 1 micron, though it is to be understood that the focal distance of the nanolight element 410 may be larger or smaller depending on the structure of the nanolight element 410 itself.

In other embodiments, the element 410 may be a noncontact grating operating in the near field (within 100 nm of the substrate surface). The grating patterns the incident light onto the surface of the layered structure with a period equivalent to the grating spacing. The pattern produced by the grating may be essentially linear in nature, e.g. a series of slits.

Collection optics (not shown) receive the beams of light 418 reflected from the sample 199 and conduct them to a suitable sensor (not shown). A suitable sensor may be an imaging device such as a CCD or CMOS camera element or photodiode array, a device such as a photo multiplier tube (PMT), photodiode, or position sensitive detector (bi-cell or quad-cell) to measure beam deflection as a result of surface displacement or lateral phase shifts. The sensor is coupled to a computer or other processor that decodes signals output by the sensor to calculate, lookup or interpolate/extrapolate at least one characteristic or parameter of the sample. As described above, the light source may be adapted to provide a pump beam of light and a probe beam of light with a selected time delay therebetween. Note that the time delays between the respective pump and probe beams of light may be selected to be a range of times that it would take a surface acoustic wave induced in the sample 199 at a selected location by a pump beam of light to travel to an adjacent location on the sample; the locations in question are defined by the pattern of the apertures 416.

Figure 9:
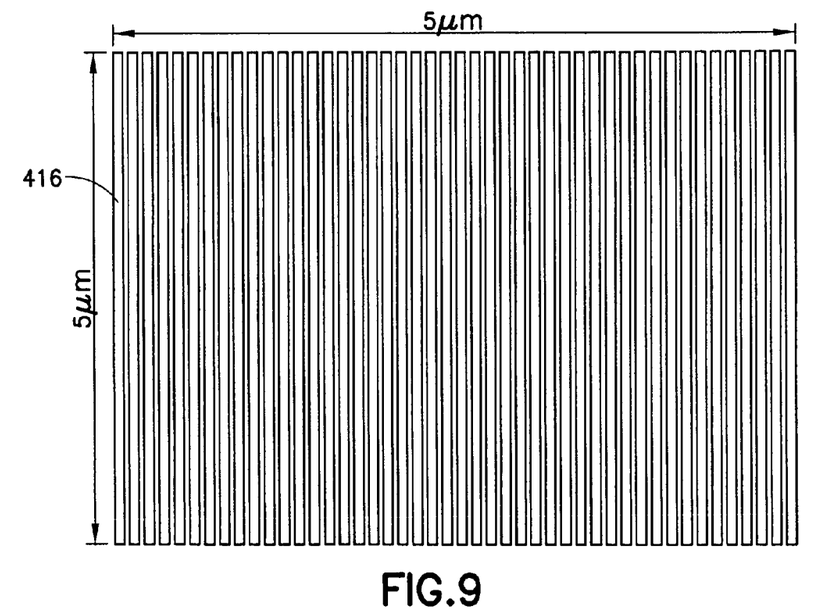
FIG. 9 is a schematic representation of a grating or an array of slits formed into a nanolight element and/or a representation of a pattern of light formed on a substrate by the grating or nanolight element.

FIG. 9 illustrates another exemplary embodiment of a nanolight element 410 that incorporates apertures 416 in the form of elongate slits in lieu of cylindrical bores. These slit apertures 416 are positioned in a one dimensional array in a substantially parallel relationship to one another. The array in the illustrated example is approximately 5 microns square. The pitch of the slit apertures 416 may be any useful dimension consistent with extraordinary optical transmission (EOT) including, for example, 100, 200, or 300 nm. The line width of the list apertures 416 may be of any useful dimension and may be selected to maximize the EOT of the system. As indicated above, many different wavelengths of light may be used, including, for example light having a wavelength of 515 nm. Extraordinary transmission is a term that may be used to describe optical elements and arrangements that have transmission efficiencies higher than standard diffraction theory would suggest is possible.

Figure 10:
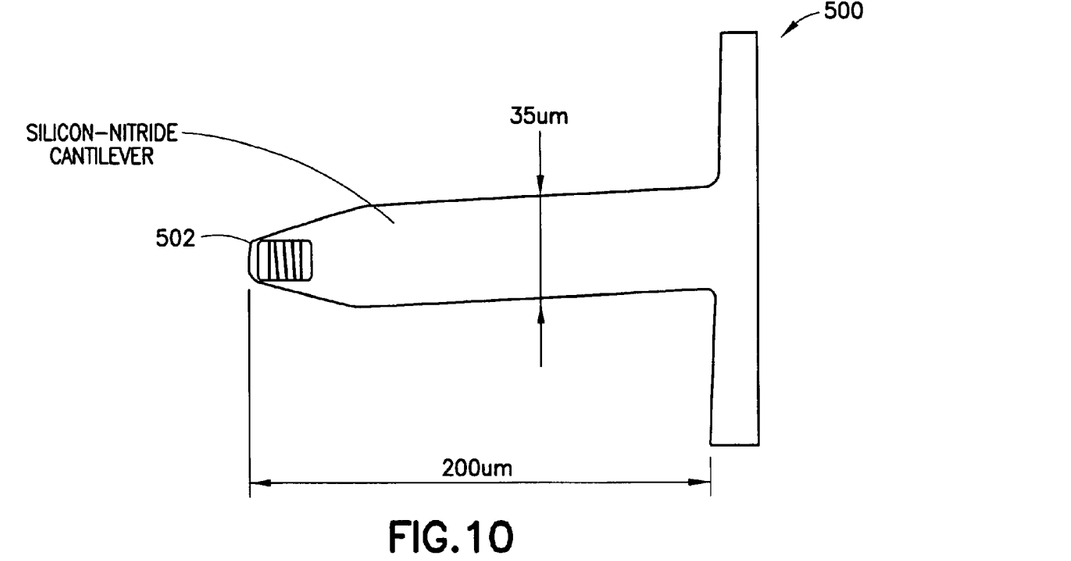
FIG. 10 illustrates a grating formed on a silicon nitride cantilever for deployment above a substrate in the analysis of surface acoustic waves.
Figure 11:
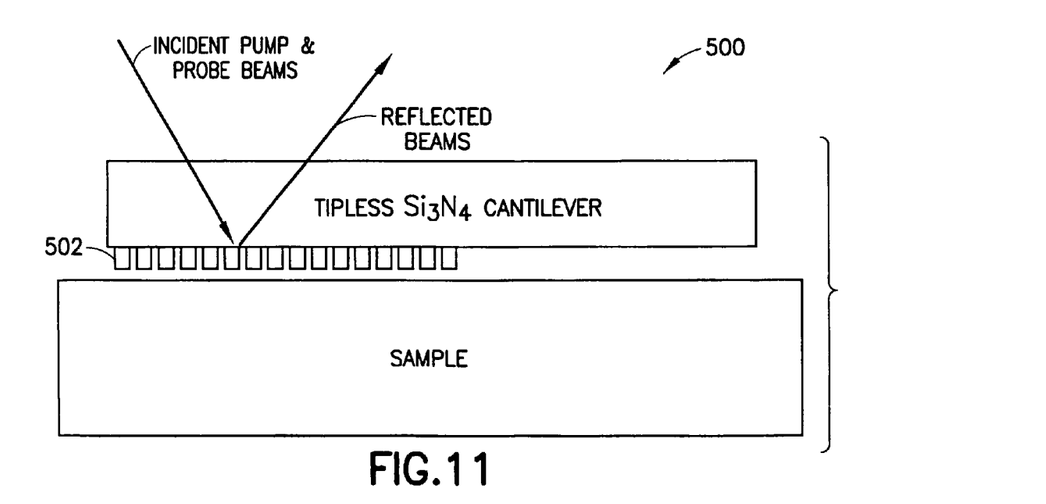
FIG. 11 is a schematic cross-section representation of the embodiment illustrated in FIG. 10.

FIG. 10 illustrates another exemplary embodiment of an optical system 500 that incorporates a grating for the measurement of surface acoustic waves. In FIG. 10 an optical element 502 is formed on the surface of a cantilever 504. In some instances the optical element may be formed as a simple grating and in other instances, the optical element may be formed as a nano-light element. As shown in FIGS. 10 and 11, the optical element 502 is a simple grating.

In FIGS. 10 and 11 the optical element 502 is shown with a series of uniformly spaced slits. In addition to or in lieu of the illustrated slits, optical element 502 may be formed with one or an array of bores of a suitable shape and size. As illustrated, the slits of the optical element 502 have a pitch that is between 50 and 500 nanometers. The pitch of the optical element 502 or any optical element constructed and arranged according to the principles in accordance with the present invention may be correlated to the wavelength of surface acoustic waves induced in the surface of a substrate that is under test. It is possible to position elements such as bores or slits of an optical element at multiples of the wavelength of the expected surface acoustic waves. It may also be possible to modify the periodicity of such slits or bores.

In one exemplary embodiment, the periodicity of an optical element 502 is modified to be discontinuous in a desired fashion. When light is incident upon the optical system 500, a resulting reflected signal will contain information from multiple frequencies or time delays. This signal may then be decoded using a suitable Fourier transform or fit in a time domain analysis to determine characteristic of the substrate under test. In another possible embodiment, multiple or variable periodicities are used in optical element 502 to obtain information about beat frequencies in the surface acoustic waves that are induced by three dimensional structures in the substrate under test. Further, optical elements 502 having multiple or variable periodicities may be used to distinguish between Rayleigh and LAM waves that have been induced in a substrate under test.

FIG. 11 is a side view of the optical system 500 of FIG. 10. Note that while illumination systems have been omitted from the figure for clarity, any useful arrangement of lasers or broadband light sources may be used to form a beam of light that may be incident upon optical element 502. In some embodiments, the optical system 500 may consist of a single optical element or grating 502 having a fixed pitch or periodicity. In other embodiments, multiple optical elements or gratings 502 each having the same or different pitches may be included. In yet other embodiments one or more of the multiple optical elements or gratings 502 may have discontinuous pitches. Illumination of each of the optical elements may be accomplished by directing a single beam of light (pump or probe beams of light as described above), onto each of the one or more optical elements 502 that are provided simultaneously. In this instance, one or more sensors may be adapted to capture information from light reflected from the one or more optical elements 502, e.g. a single sensor may spatially differentiate the signals from each of the one or more optical elements 502. In other embodiments, each optical element 502 will have a separate sensor (not shown) associated therewith.

CONCLUSION

While various examples were provided above, the present invention is not limited to the specifics of the examples.

Although specific embodiments of the present invention have been illustrated and described herein, it will be appreciated by those of ordinary skill in the art that any arrangement that is calculated to achieve the same purpose may be substituted for the specific embodiments shown. Further, many adaptations of the invention will be apparent to those of ordinary skill in the art and accordingly, this application is intended to cover any adaptations or variations of the invention. It is manifestly intended that this invention be limited only by the following claims and equivalents thereof.

What is claimed is:

1. A noncontact optical system for the analysis of surface acoustic waves comprising:

at least one pump element optically coupled to a first illumination source, the pump element being oriented to direct illumination from the first illumination source onto a substrate so as to induces a surface acoustic wave in the substrate;

the first illumination source providing illumination to the substrate through the at least one pump element to induce a surface acoustic wave in the substrate;

at least one probe element optically coupled to a second illumination source and to a photodetector, the at least one probe element being oriented to direct illumination from the second illumination source to the substrate and to conduct at least a portion of light returned from the substrate to the photodetector;

a time delay element optical coupled between the second illumination source and the probe element, the time delay element operable to vary a time delay between the illumination of the substrate by the first illumination source via the at least one pump element and the illumination of the substrate by the second illumination source via the at least one probe element; and, a processor coupled to the photodetector, the processor adapted to determine at least one substrate characteristic based at least in part on an output of the photodetector;

wherein the at least one pump element and the at least one probe element are nanolight elements; and wherein a beam of light emitted from the at least one pump element and the at least one probe element experiences diffraction that is less than $d=\lambda/2n \sin \alpha$.

2. The optical system of claim 1 wherein the at least one pump element and the at least one probe element are NSOM devices operating in the near field.

3. The optical system of claim 1 wherein the at least one pump element and the at least one probe element are gratings operating in the near field.

4. The optical system of claim 1 wherein the first and the second illumination sources are the same illumination source and are optically coupled to the at least one pump element and the at least probe element by a beam splitter that also optically couples the at least one probe element to the photodetector.

5. The optical system of claim 1 wherein light passing through the at least one pump element and the at least one probe element has a transmission efficiency of at least unity.

6. The optical system of claim 1 wherein a lateral dimension of a hole through which light may pass is less than 100 nm.

7. The optical system of claim 1 wherein a lateral dimension of a hole through which light may pass is less than 50 nm.

8. The optical system of claim 1 wherein the probe element comprises an aperture selected from a group consisting of an elongate slit and a cylindrical bore.

9. A noncontact optical system for the analysis of surface acoustic waves comprising:

one or more masking elements optically coupled to at least one source of light such that at least one first beam of light incident upon the masking element is transmitted onto a surface of a substrate to induce a surface acoustic wave in the surface of the substrate in a predetermined initial pattern;

a time delay mechanism associated with the at least one source of light such that at least one second beam of light from the at least one source of light is transmitted onto the surface of the substrate at a specified time delay with respect to the first beam of light and in substantially the same initial pattern as the first beam of light;

collection optics for collecting the at least one second beam of light reflected from the substrate, the collection optics directing the at least one second beam of reflected light to a sensor for measuring at least one characteristic of the at least one second beam of reflected light; and, a processor that receives input from the sensor and which determines from the input at least one characteristic of the substrate;

wherein the at least one light source comprises a first light source that outputs pulses of light at a substantially constant repetition rate and a second light source that outputs pulses of light at a variable repetition rate such that the difference between the frequencies of the first and second light sources comprises a range of time delays that substantially encompasses the expected times that an acoustic surface wave would take to travel between selected locations of the pump and probe light patterns.

10. The noncontact optical system of claim 9 wherein the mask element is selected from a group consisting of a grating and a nanolight element.

11. The noncontact optical system of claim 10 further comprising a plurality of masking elements of different periodicities.

12. The noncontact optical system of claim 11 wherein the at least one first beam of light is incident on at least two of the plurality of masking elements of different periodicities.

13. The noncontact optical system of claim 11 wherein the at least one second beam of light is incident on at least two of the plurality of masking elements of different periodicities.

14. The noncontact optical system of claim 11 wherein the at least one first beam of light and the at least one second beam of light have at least one distinguishing characteristic.

15. The noncontact optical system of claim 14 wherein the at least one masking element is constructed and arranged to, as a result of the incidence of the at least one first and second beams, to produce respective reflected light signals corresponding to each of the at least one first and second beams.

16. The noncontact optical system of claim 14 wherein the at least one distinguishing characteristic is selected from a group consisting of wavelength, range of wavelengths, polarization state, angle of incidence, and azimuthal angle.

17. The noncontact optical system of claim 9 wherein the mask element is comprised of a metamaterial.

18. The noncontact optical system of claim 9 wherein the mask element imposes an initial pattern by passing light from a plurality of apertures whose shape is selected from a group consisting of cylindrical bores and elongate slits.

19. The noncontact optical system of claim 9 wherein the mask element projects more than one period onto the substrate.

20. The noncontact optical system of claim 9 wherein the mask element projects more than one k-vector onto the substrate.

21. The noncontact optical system of claim 9 wherein at least one of the masking elements defines a grating having a periodicity that correlates to a wavelength of surface acoustic waves in the substrate.

22. The noncontact optical system of claim 9 wherein at least one of the masking elements has a variable periodicity.

23. The noncontact optical system of claim 22 wherein the incidence of the at least one first and second beams upon the at least one masking element produces a reflected optical signal indicative of a characteristic of at least one of a Rayleigh wave and a LAM wave in the substrate.

24. The noncontact optical system of claim 9 wherein a masking element associated with the at least one first beam has a different periodicity than a masking element associated with the at least one second beam.

25. The noncontact optical system of claim 9 wherein at least one of the masking elements defines a grating having a plurality of periodicities.

26. The noncontact optical system of claim 9 further comprising a first grating having a first periodicity and a second grating having a second periodicity, the first grating having incident thereon a first wavelength and the second grating having incident thereon a second wavelength, the first and second wavelengths being different from one another.

27. The noncontact optical system of claim 9 wherein the period of the initial pattern of light is substantially the same as the wavelength of the induced surface acoustic waves.

28. The noncontact optical system of claim 9 wherein the period of at least one of the first and second masking element varies.

29. The noncontact optical system of claim 9 comprising a plurality of masking elements, each masking element having a different periodicity.

30. A noncontact optical system for the analysis of surface acoustic waves comprising:
- one or more masking elements optically coupled to at least one source of light such that at least one first beam of light incident upon the masking element is transmitted onto a surface of a substrate to induce a surface acoustic wave in the surface of the substrate in a predetermined initial pattern;
- a time delay mechanism associated with the at least one source of light such that at least one second beam of light from the at least one source of light is transmitted onto the surface of the substrate at a specified time delay with respect to the first beam of light and in substantially the same initial pattern as the first beam of light;
- collection optics for collecting the at least one second beam of light reflected from the substrate, the collection optics directing the at least one second beam of reflected light to a sensor for measuring at least one characteristic of the at least one second beam of reflected light; and,
- a processor that receives input from the sensor and which determines from the input at least one characteristic of the substrate;
- wherein a masking element associated with the at least one first beam has a different periodicity than a masking element associated with the at least one second beam.

* * * * *